United States Patent
Dockner et al.

(10) Patent No.: US 7,276,630 B2
(45) Date of Patent: Oct. 2, 2007

(54) PROCESS FOR COUPLING BENZYLAMINES WITH HALOAROMATICS

(75) Inventors: Michael Dockner, Köln (DE); Ulrich Scholz, Mülheim an der Ruhr (DE); Torsten Neugebauer, Bad Honnef (DE)

(73) Assignee: Saltigo GmbH, Leverkusen (DE)

( * ) Notice: Subject to any disclaimer, the term of this patent is extended or adjusted under 35 U.S.C. 154(b) by 0 days.

(21) Appl. No.: 11/525,281

(22) Filed: Sep. 22, 2006

(65) Prior Publication Data

US 2007/0073078 A1    Mar. 29, 2007

(30) Foreign Application Priority Data

Sep. 28, 2005  (DE) .................. 10 2005 046 344

(51) Int. Cl.
*C07C 211/00* (2006.01)
(52) U.S. Cl. .................................. 564/384
(58) Field of Classification Search ............ None
See application file for complete search history.

(56) References Cited

U.S. PATENT DOCUMENTS 6,953,812 B2    10/2005    Jorgensen et al.

FOREIGN PATENT DOCUMENTS

WO    WO 2004/052939    6/2004

OTHER PUBLICATIONS

Kataoka et al, J. Org Chem. 2002, vol. 67 pp. 5553-5566.*
Wolfe et al; J. Org. Chem. 2000, vol. 65, pp. 1158-1174.*
Wolfe, J. P., et al.; "Simple Efficient Catalyst System for the Palladium-Catalyzed Amination of Aryl Chlorides, Bromides, and Triflates", *Journal of Organic Chemistry, American Chemical Society*, 2000, 65, pp. 1158-1174.
Kataoka, Noriyasu, et al.; "Air Stable, Sterically Hindered Ferrcenyl Dialkylphosphines for Palladium-Catalyzed C-C, C-N, and C-O Bond-Forming Cross-Coupling", *Journal of Organic Chemistry, American Chemical Society*, 2002, 67, pp. 553-5566.

* cited by examiner

*Primary Examiner*—Samuel Barts
(74) *Attorney, Agent, or Firm*—Michael A. Miller

(57) ABSTRACT

A process is provided for preparing optionally substituted arylated benzylamines from the corresponding optionally substituted aryl halides and optionally substituted benzylamines using a specific solvent mixture, a base and a catalyst comprising a palladium compound and a bisaryldialkylphosphine.

19 Claims, No Drawings

PROCESS FOR COUPLING BENZYLAMINES WITH HALOAROMATICS

FIELD OF THE INVENTION

The invention provides a process for coupling benzylamines with haloaromatics to give the corresponding arylated benzylamines using a base and a catalyst comprising a palladium compound and a bisaryldialkylphosphine.

BACKGROUND OF THE INVENTION

Arylated benzylamines find wide use as synthesis units and active substance components; see, for example, WO-A-02/00612.

It is known that arylated benzylamines can be prepared by reacting aniline derivatives with benzyl chlorides (cf. H. G. O. Becker, Organikum, 19$^{th}$ ed., Barth Dt. Verlag der Wiss. 1993, p.451, ISBN 3-335-00343-8). However, a disadvantage of this process is that correspondingly functionalized anilines and benzyl chlorides are in many cases obtainable only with difficulty.

The preparation of arylated benzylamines by means of a palladium-catalysed amination reaction of chloroaromatics is described, for example, in J. Org. Chem. 2002, 67, 5553-5566, or that of bromoaromatics in J. Org. Chem. 2000, 65, 1158-1174. The solvents used here include polar solvents, for example dimethoxyethane, or nonpolar aprotic solvents, for example toluene. However, in-house investigations have found that only incomplete conversion to the desired arylated benzylamine is achieved when some reactants are converted by the process described.

There is accordingly a need to provide a process for preparing arylated benzylamines from the corresponding haloaromatics and benzylamines.

SUMMARY OF THE INVENTION

It has been found that, surprisingly, the preparation of arylated benzylamines from the corresponding haloaromatics and benzylamines succeeds in good yields when the reaction is effected in mixtures of nonpolar aprotic solvents and polar, protic or aprotic solvents.

DETAILED DESCRIPTION OF THE INVENTION

The present invention thus provides a process for preparing compounds of the general formula (I)

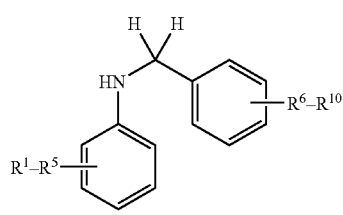

where
$R^1$ to $R^{10}$ are each independently hydrogen, $C_1$-$C_{12}$-alkyl, $C_1$-$C_{12}$-alkoxy, $C_4$-$C_{18}$-aryl or $C_5$-$C_{19}$-arylalkyl, $C_1$-$C_{12}$-alkoxy, $C_1$-$C_{12}$-fluoroalkoxy, nitrile, ester, amide, ketone, aldehyde, hydroxyl, carboxyl or fluorine, comprising reacting compounds of the general formula (II),

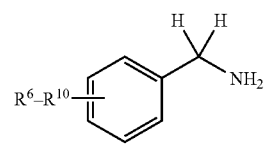

where $R^6$ to $R_{10}$ are each as defined above for the general formula (I) with compounds of the general formula (III)

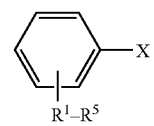

where
X is chlorine, bromine or iodine and
$R^1$-$R^5$ are each as defined above for the general formula (I), wherein the reaction is effected
in the presence of at least one palladium complex which bears, as ligands, at least one compound of the general formula (IV)

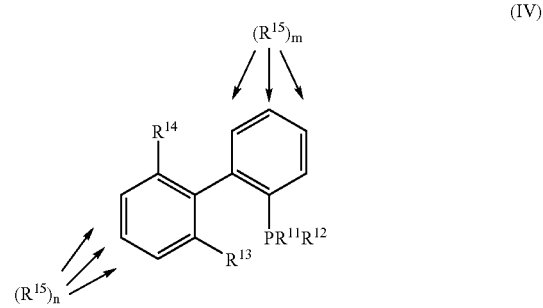

where
$R^{11}$ and $R^{12}$ are each independently $C_1$-$C_{12}$-alkyl or $C_5$-$C_{19}$-arylalkyl,
$R^{13}$ and $R^{14}$ are each independently hydrogen, $C_1$-$C_6$-alkyl, $C_1$-$C_6$-dialkylamino or $C_1$-$C_6$-alkoxy,
the $R^{15}$ radicals are each independently hydrogen, $C_1$-$C_{12}$-alkyl, $C_1$-$C_{12}$-alkoxy, $C_1$-$C_{12}$-fluoroalkyl, $C_1$-$C_{12}$-fluoroalkoxy, fluorine, $C_4$-$C_{18}$-aryl or $C_5$-$C_{19}$-arylalkyl, and the arrows indicate the possible bonding sites to the particular aryl radical, and
n and m are each independently 0, 1, 2, or 3 and
in the presence of mixtures of organic solvents comprising at least one solvent selected from the group consisting of optionally substituted aromatic hydrocarbons and at least one polar solvent and
in the presence of at least one alkali metal- or alkaline earth metal-containing base.

In the context of the invention, optionally substituted aromatic hydrocarbons are preferably understood to mean chlorine- or $C_1$-$C_6$-alkyl-substituted aromatic hydrocarbons. Suitable solvents selected from the group of optionally substituted aromatic hydrocarbons are, for example, benzene, toluene or xylene, preferably toluene.

Suitable polar solvents are in particular water, amides, for example N,N-dimethylformamide, N,N-dimethylacetamide, N-methylformanilide or N-methylpyrrolidone, ethers, for example diethyl ether, methyl tert-butyl ether, diisopropyl ether, dioxane, tetrahydrofuran, ethylene glycol dimethyl or ethylene glycol diethyl ether; alcohols, for example methanol, ethanol, n- or i-propanol, tert-butanol, ethylene glycol monomethyl ether, ethylene glycol monoethyl ether, diethylene glycol monomethyl ether or diethylene glycol monoethyl ether, or tertiary amines, for example tri-n-butylamine or triethylamine.

Preference is given to mixtures which comprise at least one polar solvent selected from water, amides, ethers, alcohols or tertiary amines.

Particular preference is given to a mixture comprising toluene and at least one polar solvent selected from N,N-dimethylformamide, N,N-dimethylacetamide, N-methylformanilide and N-methylpyrrolidone.

Especially preferred are mixtures comprising toluene and N,N-dimethylformamide.

Preference is given to using a mixture composed of at least 60% by volume of the optionally substituted aromatic hydrocarbon and at most 40% by volume of the polar solvent. In a preferred embodiment of the process, a mixture of at least two parts by volume of the aromatic hydrocarbon and at most one part by volume of the polar solvent is used. It may be particularly preferred when the polar solvent, in addition, is present in the mixture at least to an extent of 10% by volume, and the aromatic hydrocarbon to an extent of at most 90% by volume.

Especially preferably, a mixture of 70% by volume of toluene and 30% by volume of N,N-dimethylformamide is used.

The scope of the invention encompasses all radical definitions, parameters and illustrations above and listed below, in general or within areas of preference, with one another, i.e. also between the particular areas and areas of preference in any combination.

Alkyl and alkoxy each independently represent a straight-chain, cyclic, branched or unbranched alkyl and alkoxy radical respectively, and the radicals mentioned may be further substituted. The same applies to the alkylene moiety of an arylalkyl radical.

$C_1$-$C_6$-Alkyl is, for example and with preference, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl; $C_1$-$C_{12}$-alkyl is additionally, for example, n-heptyl, n-octyl, n-decyl and n-dodecyl.

$C_1$-$C_6$-Alkoxy is, for example and with preference, methoxy, ethoxy, n-propoxy, isopropoxy, n-butoxy, sec-butoxy, tert-butoxy, n-pentoxy, cyclohexoxy, cyclopentoxy, n-hexoxy; $C_1$-$C_{12}$-alkoxy is additionally, for example, n-heptoxy, n-octoxy, n-decoxy and n-dodecoxy.

Fluoroalkyl is in each case independently a straight-chain, cyclic, branched or unbranched alkyl radical, which is singly, multiply or fully substituted by fluorine atoms.

For example, $C_1$-$C_{12}$-fluoroalkyl is trifluoromethyl, 2,2,2-trifluoroethyl, pentafluoroethyl, nonafluorobutyl, heptafluoroisopropyl, perfluorooctyl and perfluorododecyl.

Aryl is either a heteroaromatic radical having 5 to 18 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen, or a carbocyclic aromatic radical having 6 to 18, preferably 6 to 10 skeleton carbon atoms.

Examples of mono-, bi- or tricyclic carbocyclic aromatic radicals having 6 to 18 skeleton carbon atoms are phenyl, biphenylyl, naphthyl, phenanthrenyl, anthracenyl or fluorenyl, mono-, bi- or tricyclic heteroaromatic radicals having 5 to 18 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen, are, for example, pyridinyl, oxazolyl, benzofuranyl, dibenzofuranyl or quinolinyl.

In addition, the carbocyclic aromatic radical or heteroaromatic radical may be substituted by up to five identical or different substituents per cycle which are selected from the group of fluorine, cyano, $C_1$-$C_{12}$-alkyl, $C_1$-$C_{12}$-fluoroalkyl, $C_1$-$C_{12}$-fluoroalkoxy, $C_1$-$C_{12}$-alkoxy or di($C_1$-$C_8$-alkyl) amino.

Arylalkyl is in each case independently a straight-chain, cyclic, branched or unbranched alkyl radical as defined above, which may be substituted singly, multiply or fully by aryl radicals as defined above. One example of arylalkyl radicals is benzyl.

The preferred substitution patterns for the general formulae (I), (II) and (III) are defined below:

$R^1$ to $R^4$ are preferably each hydrogen
$R^5$ is preferably a cyclic alkyl radical
$R^6$ to $R^9$ are preferably each hydrogen
$R^{10}$ is preferably an ester radical and
X is preferably chlorine or bromine, more preferably chlorine.

A particularly preferred compound of the general formula (I) is methyl N-(4-cyclohex-1-enylphenyl)-4-methylaminobenzoate. A particularly preferred compound of the general formula (III) is 4-cyclohex-1-enylchlorobenzene. A particularly preferred compound of the general formula (II) is methyl 4-methylaminobenzoate.

The preferred substitution patterns for the general formula (IV) are defined below:

$R^{11}$ and $R^{12}$ are each independently isopropyl, tert-butyl, cyclopentyl, or cyclohexyl, more preferably each identically the aforementioned radicals and more preferably each identically isopropyl, $R^{13}$ and $R^{14}$ are preferably each independently methyl, dimethylamino, ethyl, isopropyl and methoxy, more preferably each identically aforementioned radicals and most preferably each identically isopropyl, n is preferably 0 or 1,
m is preferably 0 and
$R^{15}$ is independently methyl, ethyl, isopropyl or methoxy.

A particularly preferred compound of the general formula (IV) is 2-dicyclohexylphosphino-2'-(N,N-dimethylamino) biphenyl.

The compounds of the general formula (IV) are known from the literature and can be prepared, for example, according to S. Kaye, J. M. Fox, F. A. Hicks, S. L. Buchwald, Adv. Synth. Catal. 2001, 343, 8, 789-794.

Useful palladium complexes which, as ligands, have at least one compound of the general formula (IV) are, for example, isolated or preformed palladium complexes containing at least one compound of the general formula (IV) or those which are obtained by reacting a palladium precursor with at least one compound of the general formula (IV) in the reaction medium. The palladium complexes used for the process are preferably obtained by reacting a palladium precursor with at least one compound of the general formula (IV).

Suitable palladium precursors are all palladium compounds which can react with compounds of the general formula (IV) to form palladium-phosphorous coordination.

Preferred palladium precursors are Pd$_2$(dibenzylideneacetone)$_3$, allylpalladium chloride or bromide, or palladium compounds of the general formula (Va)

PdY$^1_2$                                            (Va)

where y$^1$ is an anion, preferably chloride, bromide, acetate, propionate, nitrate, methanesulphonate, trifluoromethanesulphonate, acetylacetonate, allyl or cyclopentadienyl, or palladium compounds of the general formula (Vb)

PdY$^2_2$L$_2$                                       (Vb)

where y$^2$ is an anion, preferably chloride, bromide, acetate, methanesulphonate or trifluoromethanesulphonate, nonafluorobutanesulphonate, tetrafluoroborate or hexafluorophosphate, L is in each case a nitrile, preferably acetonitrile, benzonitrile or benzyl nitrile, an olefin, preferably cyclohexene or cyclooctene, or L$_2$ together is a diolefin, preferably norbornadiene or 1,5-cyclooctadiene.

Preferred palladium precursors are palladium(II) acetate or [Pd$_2$(dba)$_3$].

Especially when the palladium complexes used are obtained by reacting a palladium precursor with at least one compound of the general formula (IV) in the reaction medium, the molar ratio of palladium to compounds of the general formula (IV) may, for example, be 1 to 4, but preferably 1.5 to 3.5 and more preferably 1.8 to 3.2, in particular exactly 2.

The molar ratio of palladium to compounds of the general formula (III) may, for example, be 0.000001 to 0.05, but preferably 0.001 to 0.03 and more preferably 0.005 to 0.02.

The process according to the invention is carried out in the presence of at least one alkali metal- or alkaline earth metal-containing base. Alkali metal- or alkaline earth metal-containing bases are, for example and with preference, alkali metal or alkaline earth metal hydroxides, alkali metal or alkaline earth metal carbonates, or alkali metal or alkaline earth metal alkoxides, more preferably alkali metal or alkaline earth metal hydroxides, for example lithium hydroxide, sodium hydroxide, potassium hydroxide or calcium hydroxide, alkali metal or alkaline earth metal carbonates, for example potassium carbonate or caesium carbonate, or alkali metal alkoxides, for example sodium methoxide, sodium ethoxide, sodium n- or i-propoxide, sodium n-, i-, s- or t-butoxide, or potassium methoxide, potassium ethoxide, potassium n- or i-propoxide, or potassium n-, i-, s- or t-butoxide. Very particular preference is given to potassium phosphate, sodium hydroxide or potassium hydroxide, or sodium tert-butoxide or potassium tert-butoxide. In a preferred embodiment, potassium phosphate is used.

The molar ratio of alkali metal- or alkaline earth metal-containing base to compounds of the general formula (m) may, for example, be 0.9 to 1.5. Larger amounts are likewise possible but uneconomic. The molar ratio is preferably 1.0 to 1.4 and more preferably 1.2.

The molar ratio of the compound of the general formula (II) to compounds of the general formula (III) may, for example, be 1 to 2. Larger amounts are possible but uneconomic. The molar ratio is preferably 1.0 to 1.4 and more preferably 1.1.

The reaction temperature may, for example, be 40 to 150° C., preferably 60 to 110° C., more preferably 95 to 105° C.; the reaction pressure selected is, for example, any pressure from 0.5 to 100 bar; preference is given to ambient pressure.

Any reaction times are suitable. For example, the reaction time may be 0.5 to 48 h, preferably 4 to 24 h, more preferably 6 to 24 h.

In the inventive manner, it is possible to obtain compounds of the general formula (I) more flexibly in higher purity and/or higher yield and/or in a simpler manner than has been possible to date with the known processes described by way of introduction.

EXAMPLES

Example 1

Inventive

A 1 l flat-flanged beaker with thermometer, reflux condenser and septum is initially charged with 60 g of 1-chloro4-cyclohex-1-enylbenzene, 72 g of methyl 4-(aminomethyl)benzoate, 250 ml of toluene and 125 ml of DMF. 79.2 g of tripotassium phosphate are introduced with stirring.

The apparatus is evacuated three times and aerated again with nitrogen each time.

Subsequently, a solution of 0.7 g of palladium acetate and 2.5 g of 2-dicyclohexylphosphino-2'-(N,N-dimethylamino) biphenyl dissolved in 7.0 g of THF is added at room temperature from a round-bottomed flask via a cannula, and the mixture is heated to 110° C.

After 22 hours at 110° C., the reaction mixture is filtered at 80-90° C. The filter cake is washed twice with 100 ml each time of hot toluene (approx. 80° C.).

The filtrates are combined and washed at room temperature twice with 217 g each time of a 14% sodium chloride solution.

The organic phase is concentrated under reduced pressure. 157 g of isopropanol are added to the distillation bottoms. Heating to 60° C. affords a solution which is cooled to 20° C. over 7-8 hours. The crystallized product is filtered off. The filter cake is washed twice with 39 g each time of cold isopropanol and finally dried at 45° C. under reduced pressure.

76 g (76% of theory) of product are isolated.

Example 2

Not Inventive

A 1 l flat-flanged beaker with thermometer, reflux condenser and septum is initially charged with 60 g of 1-chloro-4-cyclohex-1-enylbenzene, 72 g of methyl 4-(aminomethyl) benzoate and 350 ml of DMF. 79.2 g of tripotassium phosphate are introduced with stirring.

The apparatus is evacuated three times and aerated again with nitrogen each time.

Subsequently, a solution of 0.7 g of palladium acetate and 2.5 g of 2-dicyclohexylphosphino-2'-(N,N-dimethylamino) biphenyl dissolved in 7.0 g of THF is added at room temperature from a round-bottomed flask via a cannula, and the mixture is heated to 110° C.

After 22 hours at 110° C., an in-process check detects only a conversion of approx. 38%, which does not change any further even in the course of prolonged stirring time. The reaction is stopped.

Example 3

Not Inventive

A 1 l flat-flanged beaker with thermometer, reflux condenser and septum is initially charged with 60 g of 1-chloro-4-cyclohex-1-enylbenzene, 72 g of methyl 4-(aminomethyl) benzoate and 350 ml of toluene. 79.2 g of tripotassium phosphate are introduced with stirring.

The apparatus is evacuated three times and aerated again with nitrogen each time.

Subsequently, a solution of 0.7 g of palladium acetate and 2.5 g of 2-dicyclohexylphosphino-2'-(N,N-dimethylamino) biphenyl dissolved in 7.0 g of THF is subsequently added at room temperature from a round-bottomed flask via a cannula, and the mixture is heated to 110° C.

After 22 hours at 110° C., the reaction mixture is filtered at 80-90° C. The filter cake is washed twice with 100 ml each time of hot toluene (approx. 80° C.).

The filtrates are combined and washed at room temperature twice with 217 g each time of a 14% sodium chloride solution.

The organic phase is concentrated under reduced pressure. 157 g of isopropanol are added to the distillation bottoms. Heating to 60° C. affords a solution which is cooled to 20° C. over 7-8 hours. The crystallized product is filtered off. The filter cake is washed twice with 39 g each time of cold isopropanol and finally dried at 45° C. under reduced pressure.

41 g (41% of theory) of product are isolated.

What is claimed is:

1. A process for preparing compounds of the general formula (I)

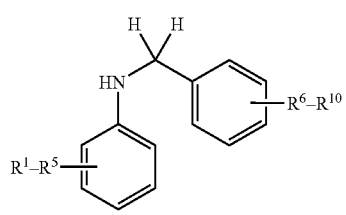

where
R$^1$ to R$^{10}$ are each independently hydrogen, C$_1$-C$_{12}$-alkyl, C$_1$-C$_{12}$-alkoxy, C$_4$-C$_{18}$-aryl or C$_5$-C$_{19}$-arylalkyl, C$_1$-C$_{12}$-alkoxy, C$_1$-C$_{12}$-fluoroalkoxy, nitrile, ester, amide, ketone, aldehyde, hydroxyl, carboxyl or fluorine,
comprising reacting compounds of the general formula (II),

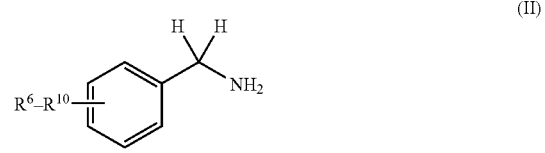

where R$^6$ to R$^{10}$ are each as defined above for the general formula (I) with compounds of the general formula (III)

where
X is chlorine, bromine or iodine and
R$^1$-R$^5$ are each as defined above for the general formula (I),
wherein the reaction is effected
in the presence of at least one palladium complex which bears, as ligands, at least one compound of the general formula (IV)

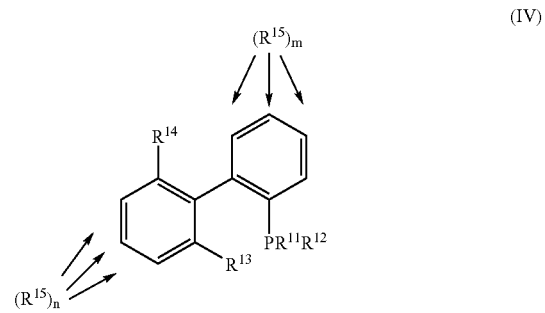

where
R$^{11}$ and R$^{12}$ are each independently C$_1$-C$_{12}$-alkyl or C$_5$-C$_{19}$-arylalkyl,
R$^{13}$ and R$^{14}$ are each independently hydrogen, C$_1$-C$_6$-alkyl, C$_1$-C$_6$-dialkylamino or C$_1$-C$_6$-alkoxy,
the R$^{15}$ radicals are each independently hydrogen, C$_1$-C$_{12}$-alkyl, C$_1$-C$_{12}$-alkoxy, C$_1$-C$_{12}$-fluoroalkyl, C$_1$-C$_{12}$-fluoroalkoxy, fluorine, C$_4$-C$_{18}$-aryl or C$_5$-C$_{19}$-arylalkyl, and the arrows indicate the possible bonding sites to the particular aryl radical, and
n and m are each independently 0, 1, 2, or 3 and
in the presence of mixtures of organic solvents comprising at least one solvent selected from the group consisting of optionally substituted aromatic hydrocarbons and at least one polar solvent and
in the presence of at least one alkali metal- or alkaline earth metal-containing base.

2. The process according to claim 1, wherein the mixture of organic solvents comprises at least one polar solvent selected from water, amides, ethers, alcohols or tertiary amines.

3. The process according to claim 1 or 2, wherein the mixture of organic solvents comprises at least one aromatic hydrocarbon selected from benzene, toluene and xylene.

4. The process according to claim 1, wherein the mixture consists of 70% by volume of toluene and 30% by volume of N,N-dimethylformamide.

5. The process according to claim 1, wherein the mixture of organic solvents contains at least 60% by volume of the aromatic hydrocarbon and at most 40% by volume of the polar solvent.

6. The process according to claim 1, wherein the palladium complexes used which bear, as ligands, at least one compound of the general formula (IV) are those which are obtained by reacting a palladium precursor with at least one compound of the general formula (IV) in the reaction medium.

7. The process according to claim 1, wherein the molar ratio of palladium to compounds of the general formula (IV) is 1 to 4.

8. The process according to claim 7, wherein the molar ratio of palladium to compounds of the general formula (IV) is 1.5 to 3.5.

9. The process according to claim 7, wherein the molar ratio of palladium to compounds of the general formula (IV) is 1.8 to 3.2.

10. The process according to claim 7, wherein the molar ratio of palladium to compounds of the general formula (IV) is exactly 2.

11. The process according to claim 1, wherein the molar ratio of palladium to compounds of the general formula (III) is 0.000001 to 0.05.

12. The process according to claim 11, wherein the molar ratio of palladium to compounds of the general formula (III) is 0.001 to 0.03.

13. The process according to claim 11, wherein the molar ratio of palladium to compounds of the general formula (III) is 0.005 to 0.02.

14. The process according to claim 1, wherein the alkali metal- or alkaline earth metal-containing bases used are alkali metal or alkaline earth metal hydroxides, alkali metal or alkaline earth metal carbonates, or alkali metal or alkaline earth metal alkoxides.

15. The process according to claim 1, wherein the molar ratio of alkali metal- or alkaline earth metal-containing base to compounds of the general formula (III) is 0.9 to 1.5.

16. The process according to claim 1, wherein the molar ratio of alkali metal- or alkaline earth metal-containing base to compounds of the general formula (III) is 1.0 to 1.4.

17. The process according to claim 1, wherein the molar ratio of alkali metal- or alkaline earth metal-containing base to compounds of the general formula (III) is 1.2.

18. Process according to claim 1, wherein the molar ratio of compounds of the general formula (II) to compounds of the general formula (III) is 1 to 2.

19. Process according to claim 1, wherein the molar ratio of compounds of the general formula (II) to compounds of the general formula (III) is 1.0 to 1.4.

* * * * *